United States Patent [19]

Scholl et al.

[11] Patent Number: 4,929,710
[45] Date of Patent: May 29, 1990

[54] HYDROXYCARBOXYLIC ACID/UNSATURATED AROMATIC HYDROCARBON RESIN USEFUL AS RECORDING MATERIAL

[75] Inventors: Thomas Scholl, Meerbusch; Gert Jabs, Odenthal, both of Fed. Rep. of Germany; Adolf Richartz, Apapa, Nigeria

[73] Assignee: Bayer Aktiengesellschaft, Leverkusen, Fed. Rep. of Germany

[21] Appl. No.: 105,799

[22] Filed: Oct. 7, 1987

[30] Foreign Application Priority Data

Oct. 21, 1986 [DE] Fed. Rep. of Germany ....... 3635742

[51] Int. Cl.$^5$ .............................................. C08G 83/00
[52] U.S. Cl. .................... 528/205; 503/200; 503/210; 528/206; 528/207; 528/392; 528/397
[58] Field of Search ............... 528/397, 205, 206, 207, 528/392

[56] References Cited

U.S. PATENT DOCUMENTS

| | | | |
|---|---|---|---|
| 3,004,953 | 10/1961 | Sonnabend | 528/205 |
| 3,657,430 | 4/1972 | Tsung-Ying Shen et al. | 424/230 |
| 3,924,027 | 12/1975 | Saito et al. | 427/147 |
| 4,357,459 | 11/1982 | Runavot et al. | 528/205 |
| 4,701,517 | 10/1987 | Daughenbaugh | 528/205 |

*Primary Examiner*—Harold D. Anderson

[57] ABSTRACT

Hydroxycarboxylic acid derivatives of the formula

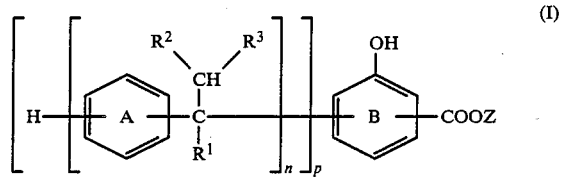

are particularly suitable for use as color developers in recording materials.

6 Claims, No Drawings

HYDROXYCARBOXYLIC ACID/UNSATURATED AROMATIC HYDROCARBON RESIN USEFUL AS RECORDING MATERIAL

The present invention relates to hydroxycarboxylic acid derivatives and to their use in pressure- or heat-sensitive recording materials (reactive recording systems).

Reactive recording systems for the purposes of the invention are in particular papers on which visible representations can be produced by imagewise mechanical pressure or by imagewise heating.

These include the known reactive copying papers (cf. M. Gutcho, Capsule Technology and Microencapsulation, Noyes Data Corporation, 1972, pages 242–277; G. Baxter in Microencapsulation, Processes and Applications, edited by J.E. Vandegaer, Plenum Press New York, London, pages 127–143).

Reactive copying papers consist for example of two or more loosely superposed sheets of paper, where in each case the upper sheet contains a donor layer on the reverse side and the lower contains an acceptor layer on the front side. Thus in each case a donor layer and an acceptor layer are in contact with each other. The donor layer contains for example microcapsules whose core material is a solution of a dyestuff former in an organic solvent and the acceptor layer contains a colour developer, i.e. a material which converts the dyestuff former into the dyestuff. A copy is produced when the microcapsules are destroyed by the pressure of a writing implement and the dyestuff former undergoes an imagewise reaction with the colour developer.

If the dyestuff former is embedded not in microcapsules but in a meltable wax, a copy is produced on subjecting the paper to imagewise heating. In this case the system is a thermoreactive recording system.

The dyestuff former and the colour developer can also have been applied to the same sheet of paper. This is then referred to as "self-contained paper". On such material it is possible to produce for example a script by imagewise pressure or imagewise heating.

Thermoreactive recording systems are preferably used in electronic computers, teleprinters, telex machines and measuring instruments. Markings can also be produced thereon by means of laser beams.

Thermoreactive recording systems can be constructed in such a way that the dyestuff former is dissolved or dispersed in a binder layer and, in a second layer, the colour developer is dissolved or dispersed in the same binder. However, dyestuff former and colour developer can also be dispersed in one layer. The binder is softened by heat and comes into contact with the colour developer in the areas where heat is applied. In the course of the coming into contact, the colour develops.

Typical examples of known colour developers are active clay substances, such as attapulgus clay, acid clay, bentonite or montmorillonite; and also halloysite, zeolite, silicon dioxide, aluminium oxide, aluminium sulphate, aluminium phosphate, zinc chloride, kaolin and other clays or acidic organic compounds, such as, for example, ring-substituted phenols, salicylic acid, metal salts of salicylic acid or esters thereof, and also acidic polymeric materials, such as phenolic polymers, alkylphenol-acetylene resins, maleic acid/colophony resin or partially or completely hydrolysed polymers of maleic anhydride and styrene, ethylene or vinyl methyl ether or polyacetals.

The colour developers can additionally also be used in mixture with inherently unreactive or not very reactive pigments or further auxiliaries such as silica gel. Examples of such pigments are: talcum, titanium dioxide, zinc oxide, chalk; clays such as kaolin and also organic pigments, for example urea-formaldehyde or melamine-formaldehyde condensation products.

Activated clays are moisture-sensitive, i.e. the developed colour can be removed with water or is only very weak in a moist atmosphere. The development of black fluoran dyestuffs, such as, for example, 3-diethylamino-6-methyl-7-anilinofluoran or 3-(N-cyclohexyl-N-methylamino)-6-methyl-7-anilinofluoran, is not possible. On the contrary, corresponding organic colour formers produce reddish black or greenish black images which rapidly fade to become reddish brown.

DE-A-2,242,250 and BE Patent Specifications 784,913 and 802,914 describe metal salts of substituted hydroxyarylcarboxylic acids, for example of salicylic acid, for use as colour developers. DE-A-2,348,639 in addition discloses mixtures of aromatic carboxylic acids or of salts thereof with polymers. The aromatic carboxylic acids and salts thereof are frequently soluble in water, which is why, on applying the aqueous print paste, a portion of the acids diffuses into the interior of the sheet, wherefrom a lower colour-forming capacity and hence a lower colour density result.

EP-A-0,181,283 already discloses metal salicylates and their use in recording materials. However, they are monomeric and crystalline compounds having a relatively high melting point.

Phenols for use as colour developers are described for example in U.S. Patent Specification No.3,244,550, phenolic resins for example in U.S. Pat. No. 3,672,935 and finally the specific use of bisphenol A resins, for example, in JA Patent Specification No. 063,958.

Phenols and phenolic resins which at present correspond to the state of the art have in particular the following disadvantages:

The copy exhibits—for example compared with clay developers—a lower intensity or depth of colour.

The rate of development of the copy is low. At the start the copy remains pale until the intensity gradually increases in the course of time.

Coated colour developer papers have a pronounced yellowness tendency, which is even enhanced by sunlight but also by artificial light sources.

The invention provides compounds of the following formula (I)

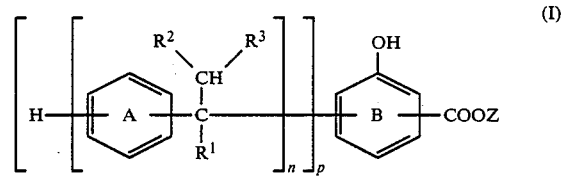

wherein the rings A and B can have further substituents and wherein $R^1$ to $R^3$ independently of one another denote H or alkyl (in particular having 1 to 4 C atoms) or together with at least 2 C atoms of the ring A denote the remainder to complete a carbocyclic ring in particular, Z denotes $M^{m+}/m$ M denotes an m-valent metal ion, in particular $Cu^{2+}$, $Zn^{2+}$, $Fe^{2+}$, $Fe^{3+}$, $Al^{3+}$, $Mg^2$ or $Ca^{2+}$ m denotes a whole number, in particular 2 or 3, n denotes a whole number, at least 2, in particular 2 to 30, especially 3 to 6, and p denotes a whole number from 1 to 3.

In a particularly preferred embodiment, the compounds of the above-indicated formula (II) conform to the following structure

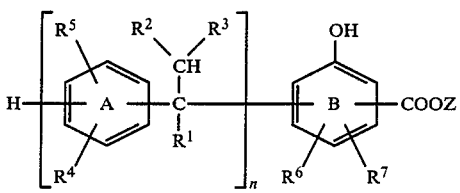

wherein $R^1$ to $R^3$, Z, M, m and n have the abovementioned meaning and wherein $R^4$ to $R^7$ independently of one another denote hydrogen, alkyl, in particular having 1 to 18 C atoms, aralkyl, in particular benzyl, halogen, and in particular hydroxyl, alkoxy, in particular having 1 to 24 C atoms, COOH, —$COOR^8$, CN, $NO_2$ or —O—CO—$R^{11}$ or cycloalkyl, it being also possible for $R^6$ and $R^7$ to denote independently of each other

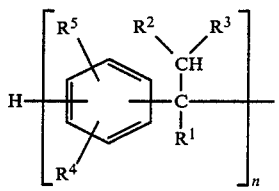

$R^8$ denotes alkyl, in particular having 1 to 24 carbon atoms, aryl, in particular phenyl or $NR^9R^{10}$, $R^9$ and $R^{10}$ independently of each other denote hydrogen, alkyl, in particular having 1 to 24 carbon atoms, and $R^{11}$ denotes alkyl, in particular $C_1$-$C_{18}$.

In a particularly preferred embodiment, the group COOZ is in the ring B in the o-position relative to the OH group.

The invention further provides a process for preparing resinous hydroxycarboxylic acids and derivatives thereof by reaction of compounds of the formula (III)

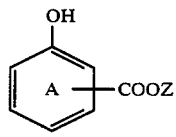   (III)

with compounds of the formula (IV)

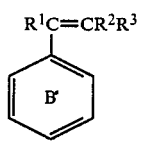

wherein the rings A and B can be substituted and Z as well as $R^1$ to $R^3$ have the above-stated meaning, characterized in that compounds III and IV are made to react at temperatures of 50° to 150° C. in the presence of acid catalysts and then reacted at the same temperature with a metal salt of an aliphatic carboxylic acid.

In a particularly preferred form of the process according to the invention, the compound of the formula (III) conforms to the following structure

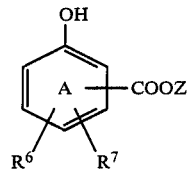

and the compound of the formula (IV) to the following structure

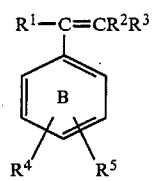

wherein Z and $R^1$ to $R^7$ have the above-stated meaning.

The invention further provides reactive recording materials which contain compounds of the formula I.

The invention further provides a process for making recordings with a reactive recording system by means of a colour developer, wherein the colour developer conforms to the above-stated formula (I) and/or is obtainable by the process according to the invention.

The metal salts according to the invention of reaction products of aromatic hydroxycarboxylic acids (III) with vinylbenzene derivatives (IV) are prepared by heating the components in the presence of acid catalysts and addition of metal salts at temperatures of 40° to 170° C. The catalysts used are Brönsted acids such as $H_2SO_4$ and p-toluenesulphonic acid.

The products according to the invention are preferably colourless to pale yellow resins having softening points of 25° to 125° C., acid values of 20 to 200 and possess average molecular weights of 300 to 3000.

Preferred starting compounds (III) are salicylic acid, p-hydroxybenzoic acid, 3-nonylsalicylic acid, 5-tert.octylsalicylic acid, 3-methyl-5-tert.-amylsalicylic acid, 3-methyl-5-tert.-octylsalicylic acid, 3-cyclohexyl-5ethylsalicylic acid, 5-chlorosalicylic acid, 2,4-dihydroxybenzoic acid.

Preferred starting compounds (II) are styrene, 4chlorostyrene, 4-methylstyrene, 4-hydroxystyrene, α-methylstyrene, indene.

It is of course also possible to use mixtures of the starting materials described.

The reaction components can be varied within wide limits. Preferred products result from molar ratios (III): (IV) = 1:2-8. The catalyst concentration can likewise be varied within wide limits. To obtain uniform products, however, it is desirable to minimize the catalyst concentration (about 0.5 to 3% by weight, relative to compound (IV).

Particularly suitable catalysts are Brönsted acids. These are in particular sulphuric acid and p-toluenesulphonic acid, dodecylbenzenesulphonic acid, hydrochloric acid and the like. The advantage of Brönsted acids over Lewis acids such as $AlCl_3$, $BF_3$, $SnCl_4$, $TiCl_4$, with which the reaction is admittedly also possible, is the light-coloured-ness of the products which is essential for the use as colour developers in reactive writing systems.

The metal salts used are transition metal salts and also salts of main groups II and III of the periodic table of the elements. It is advisable to use metal salts of weak organic acids, such as, for example, acetates, propionates, butyrates etc. Preference is given to acetates of zinc, Fe, Mg, Ca, Al. Of these, the zinc salt is particularly preferred.

To prepare the products according to the invention, it is expedient to introduce the aromatic hydroxycarboxylic acids in the pure form or in an inert solvent, such as chlorobenzene, together with the Brönsted acid, for example sulphuric acid, first and to add the vinylbenzene compound (IV) at temperatures of 40° to 170° C., preferably 60° to 120° C. A metal salt, preferably a metal acetate, is then added, and in the case of metal acetates, acetic acid is distilled off.

The resin thus prepared can be washed at this stage by adding a solvent and water. Residual traces of acid catalyst have barely any effect on the colour-developing properties of the products, so that the wash with water is frequently superfluous. It is more important to maintain the upper temperature limit of at most 170° C., since at higher temperatures the resin undergoes a slow decarboxylation, which goes hand in hand with losses of colour developer properties.

The colour developers according to the invention and the aqueous dispersions described can be used for example for preparing carbon-free copying papers and for preparing thermoreactive recording materials. To this end, the dispersions of the colour developers according to the invention are spread-coated onto a paper carrier web. The formulation of such spread-coating inks is known.

A spread-coating ink to be used for preparing a carbon-free copy paper can be effected for example by mechanical dispersing of the resin powder in water which contains sufficient quantities of dispersant.

Suitable dispersants are for example polyvinyl acetates, polyvinyl alcohols, hydroxyethylcellulose, gum arabic, guar gum, locust bean gum or gum ghatti. Particular preference is given to dispersions which, in addition to the colour developers according to the invention, contain combinations of various polysaccharides: gum arabic and guar gum, gum arabic and locust bean gum; evidently the gum arabic acts here as a dispersant, while the other polysaccharide acts as a thickener, preventing resin particles from sedimenting and agglomerating.

Suitable mechanical dispersing means are commercially available colloid mills, bead mills, ball mills and similar homogenizing devices.

To effect further formulation of the spread-coating inks, the aqueous dispersion frequently has added to it absorbents such as chalk, spread-coating clay, aluminium silicates etc.

The colour-developing properties of the colour developers according to the invention are particularly advantageous if they are used as "hybrid systems", i.e. if they are combined for example with chemically modified aluminium layer silicates based on montmorillonite.

In addition, the spread-coating inks must be provided with binders to fix the colour developers on a carrier. Since paper is the preferred carrier material, the binders are chiefly paper-coating agents, such as gum arabic, polyvinyl alcohol, hydroxymethylcellulose, casein, methylcellulose, dextrin, starch, starch derivatives or polymer latexes. The latter are for example butadienestyrene copolymers or acrylic monopolymers or copolymers.

The spread-coating compositions containing the colour donors according to the invention permit the use of various known coating techniques, for example application by means of a blade coater or other customary coating techniques.

In addition to aqueous spread-coating inks, however, incorporation is also possible into printing inks for flexographic or offset printing.

In the preparation of an offset or letterpress printing ink, the developer resins according to the invention can be ground with a suitable varnish on a three-roll mill. The preparation of such offset printing inks is known state of the art.

Flexographic printing inks contain in addition to binders a low-boiling solvent. Suitable solvents for this purpose are for example $C_1-C_6$-alcohols, $C_2-C_4$-alkanediols, $C_2-C_4$-alkanetriols, ethylene glycol monoalkyl ethers, aromatic hydrocarbons, esters and/or ketones. Solvents also include methanol, ethanol, n-propanol, isopropanol, n-butanol, isobutanol, sec.-butanol, ethylene glycol monomethyl ether, ethylene glycol, 1,2-propanediol, glycerol, acetone, methyl ethyl ketone, toluene, xylene or mixtures thereof. The preparation of flexographic printing inks is likewise long-known state of the art.

The printing inks can be applied spotwise to certain zones of the carrier material, for example using offset or flexographic printing equipment.

Using this process it is possible to produce spotcoated developer papers, and the hitherto customary, zonewise neutralizing of a whole-area-coated developer in those areas where for security reasons no copy is to be produced can be dispensed with.

The developer resins according to the invention can likewise be used for preparing thermo papers.

Thermoreactive recording systems encompass for example heat-sensitive recording and copying materials and papers. These systems are used for example for recording data, for example in electronic computers, teleprinters, telex machines or in recorders and measuring instruments, such as, for example electrocardiographs. Image production (marking) can also be effected manually by means of a hot pen. A further way of producing markings by means of heat are laser beams.

The thermoreactive recording material can be constructed such that the colour former is dissolved or dispersed in a binder layer and in a second layer the developer is dissolved or dispersed in the binder. Another possibility is that both the colour former and the developer are dispersed in one layer. The binder is softened in specific areas by means of heat and, at the points where heat is applied, the colour former comes into contact with the developer and the desired colour develops immediately.

The preparation of thermopapers is known state of the art.

In the preparation and application examples which follow, the percentages given, unless otherwise stated, are by weight, and parts are parts by weight.

EXAMPLES

Example 1

A mixture of 552 g of salicylic acid and 20 g of concentrated $H_2SO_4$ in 1200 ml of chlorobenzene has added to it at about 50-60° C. 1248 g of styrene. The resulting clear solution is subsequently stirred for 3 hours, cooled down to 130° C. and has added to it at 50° C. 438 g of $Zn(OAc)_2 \times 2\ H_2O$. All the solvent is then distilled off in vacuo. This gives 1924 g of a slightly yellowish resin having a softening point of 45° C., an acid value of 117, an OH value of 194-204, an average molecular weight of 430 (by GPC).

Example 2

A mixture of 35 g of salicylic acid and 104 g of p-chlorostyrene has added to it at room temperature 2.5 g of concentrated $H_2SO_4$, whereupon the exothermic reaction sets in. This is followed by heating at 130° C. for a further 4 hours, addition of 27 g of $Zn(OAc)_2 \times 2\ H_2O$ at 100° C. and removal by distillation of all the volatile constituents in vacuo. This gives about 140 g of a yellowish resin having a softening point of 74° C., an OH value of 185, an average molecular weight of 400 (by GPC).

Example 3

Example 2 is repeated reacting 35 g of salicylic acid in the presence of 2.5 g of concentrated $H_2SO_4$ with 207.8 g of p-chlorostyrene and 27 g of $Zn(OAc)_2 \times 2\ H_2O$. Yellowish resin having a softening point of 98° C.

Example 4

A mixture of 97.5 g of 5-tert.-butylsalicyclic acid and 5 g of concentrated $H_2SO_4$ in 80 ml of chlorobenzene has added to it at 50° C. 208 g of styrene, after 3 hours of subsequent stirring at 130° C. 54.9 g of $Zn(OAc)_2 \times 2\ H_2O$ are added at 100° C., and all the volatile constituents are distilled off in vacuo. This gives a greyish transparent resin having a softening point of 49° C.

Example 5

Example 1 is repeated reacting a mixture of 27.6 g of salicylic acid and 2 g of concentrated $H_2SO_4$ in 100 ml of chlorobenzene with 208 g of styrene and 21.9 g of $Zn(OAc)_2 \times 2\ H_2O$. Colourless flexible resin, OH value 70.

Example 6

Example 1 is repeated reacting a mixture of 3036 g of salicylic acid and 515 g of dodecylbenzenesulphonic acid in 3300 ml of chlorobenzene with 6864 g of styrene and 2895 g of $Zn(OAc)_2 \times 2\ H_2O$. Colourless resin having a softening point of 40° C. and an average molecular weight of 400 (by GPC).

Example 7 (for preparing a resin emulsion)

50 parts of the resin according to Example 1 were ball-milled together with 49 parts of a 10% strength aqueous polyvinyl alcohol solution (Mowiol ® 26/88 from Hoechst) and 1 part by weight of a formaldehyde condensate of a naphthalenesulphonic acid until the resin had a particle size of about 2 μm.

The result obtained was a highly viscous dispersion which was 50% resin and can be used for preparing an aqueous spread-coating ink formulation.

Example 8

10.6 kg of water were introduced first and brought to pH 9 with sodium hydroxide solution. 2.6 kg of china clay SPS and 0.9 kg of precipitated aluminium silicate were added with thorough stirring.

To 8.5 kg of the filler dispersion thus prepared is added 1 kg of the 50% strength resin emulsion according to Example 7. Once the spread-coating ink had become homogeneous through stirring, 320 g of a 50% strength styrenebutadiene latex were added.

Example 9 (Preparation of carbon-free copying papers)

Using a 40 μm wire-wound draw bar the spread-coating ink according to Example 8 was applied to a base paper having a weight per unit area of 45 g/m². The coating weight was 5-6 g/m² after drying.

The developer paper thus prepared is brought into contact with the coated side of a commercially available copying paper coated with capsules. After writing through, for example by means of a typewriter, the result is a deeply coloured copy in black or blue ink, depending on the type used.

Example 10

2.5 parts of resin of Example 2, pulverized to below 2 μm, were stirred into 6 parts of print varnish (brilliant gloss overprinting lacquer from Gebr. Schmidt, Frankfurt) by means of a kneader. The mixture was ground 5 times in a three-roll mill.

The printing ink thus formulated was applied to a paper carrier by means of an offset machine (Rotaprint). When in contact with a commercially available carbon-free copying paper, the pressure of writing produced a copy in the printed areas.

Example 11

100 g of colour donor (for example crystal violet lactone) are ball-milled with 750 g of a 6% strength aqueous solution of polyvinyl alcohol (Moviol ® 26/88 from Hoechst) down to a particle size of 2-4 μm.

8 parts of this dispersion were mixed with 60 parts of the spread-coating ink of Example 8.

The mixture is applied with a wire-wound draw bar (40 μm) to a base paper having a weight per unit area of 52 g/m². The weight of the coating was 3 and 4 g/m².

Inking the colourless paper produces at about 120° C. a blue coloration which reaches its full depth of shade at about 200° C.

We claim:

1. A compound of the following formula (I)

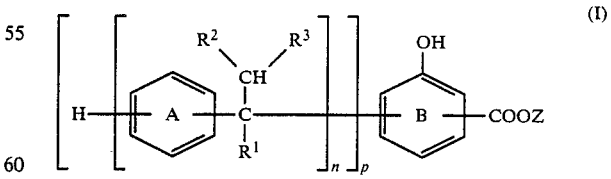

wherein the rings A and B are unsubstituted or substituted and wherein $R^1$ to $R^3$ independently of one another denote H or alkyl or together with at least 2 C atoms of ring A denote the remainder to complete a ring, Z denotes M/m M denotes an m-valent metal ion, m denotes a whole number,
n denotes a whole, at least 2 and
p denotes a whole number from 1 to 3.

2. A compound according to claim 1, having the following formula (II)

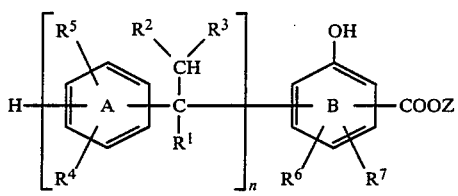

wherein
R⁴ to R⁷ independently of one another denote hydrogen, alkyl, aralkyl, halogen, alkoxy, COCH, —COOR⁸, CN, NO₂ or —O—CO—R¹¹ or cycloalkyl, or R⁶ and R⁷ each independently denote a substituent of the formula

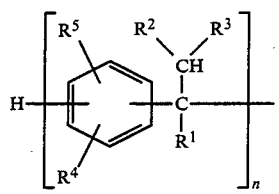

R⁸ denotes alkyl, aryl, or NR⁹R¹⁰
R⁹ and R¹⁰ independently of each other denote hydrogen or alkyl and
R¹¹ denotes alkyl.

3. A compound according to claim 2 wherein the group COOZ is attached to Ring B in the o-position relative to the OH group.

4. A process for preparing a resinous hydroxycarboxylic acid and derivatives thereof according to claim 1 by reacting at least one compound of the formula (III)

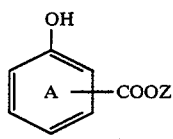

with at least one compound of the formula (IV)

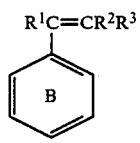

wherein the rings A and B are unsubstituted or substituted and wherein
R¹ to R³ independently of one another denote H or alkyl or together with at least 2 C atoms of ring A denote the remainder to complete a ring,
Z denotes M/m
M denotes an m-valent metal ion,
m denotes a whole number,
n denotes a whole at least 2 and
p denotes a whole number from 1 to 3
said reaction is conducted at temperatures of 50° to 150° C. in the presence of acid catalysts and then the reaction is continued at the same temperature with a metal salt of an aliphatic carboxylic acid.

5. A process according to claim 4, wherein M is Zn²⁺.

6. A process according to claim 4, wherein the compound of the formula (III) has the following formula

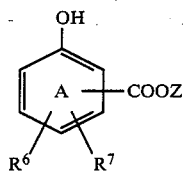

and the compound of the formula (IV) has the following formula

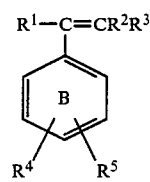

wherein
R⁴ to R⁷ independently of one another denote hydrogen, alkyl, aralkyl, halogen, alkoxy, COOH, —COOR⁸, CN, NO₂ or —O—CO—R¹¹ or cycloalkyl, or R⁶ and R⁷ each independently denote a substituent of the formula

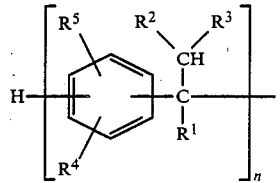

R⁸ denotes alkyl, aryl, or NR⁹R¹⁰
R⁹ and R¹⁰ independently of each other denote hydrogen or alkyl and
R¹¹ denotes alkyl.

* * * * *